| United States Patent [19] | [11] Patent Number: 5,629,018 |
| Besemer et al. | [45] Date of Patent: May 13, 1997 |

[54] COMPOSITION FOR CONTROLLED RELEASE OF AN ACTIVE SUBSTANCE AND METHOD FOR THE PREPARATION OF SUCH A COMPOSITION

[75] Inventors: Arie C. Besemer, Amerongen; Jan P. Van Der Lugt, Amersfoort, both of Netherlands

[73] Assignee: Nederlandse Organisatie voor Toegepast-Natuurwetenschappelijk Onderzoek TNO, Delft, Netherlands

[21] Appl. No.: 362,442

[22] PCT Filed: Jul. 2, 1993

[86] PCT No.: PCT/NL93/00138

§ 371 Date: Feb. 15, 1995

§ 102(e) Date: Feb. 15, 1995

[87] PCT Pub. No.: WO94/01091

PCT Pub. Date: Jan. 20, 1994

[30] Foreign Application Priority Data

Jul. 3, 1992 [NL] Netherlands ............................ 9201196

[51] Int. Cl.$^6$ ........................................ A61K 9/16
[52] U.S. Cl. .................... 424/488; 424/489; 424/468; 424/469; 424/470; 514/778; 514/965

[58] Field of Search ............................... 424/488, 465, 424/484, 468, 469, 489, 470

[56]  References Cited

U.S. PATENT DOCUMENTS 3,493,652  2/1970  Hartman ................................. 424/94

FOREIGN PATENT DOCUMENTS 63-104925   5/1988  Japan .
WO89/00601  1/1989  WIPO .
WO89/00045  1/1989  WIPO .

*Primary Examiner*—Thurman K. Page
*Assistant Examiner*—James M. Spear
*Attorney, Agent, or Firm*—Young & Thompson

[57] ABSTRACT

In a composition for delayed release of an active substance, the active substance is incorporated in a polysaccharide matrix which consists of an essentially crystalline straight-chain glucan and contains a glucan-degrading agent. The glucan is in particular an α-glucan which has essentially a helix structure. The glucan-degrading agent is preferably α-amylase. The composition can contain high-molecular materials such as proteins, allergens, vaccine substances and microorganisms, and preferably has the form of compressed tablets.

16 Claims, No Drawings

COMPOSITION FOR CONTROLLED RELEASE OF AN ACTIVE SUBSTANCE AND METHOD FOR THE PREPARATION OF SUCH A COMPOSITION

BACKGROUND OF THE INVENTION

1. Field of the Invention

The invention relates to a composition for delayed release of an active substance in a target environment, the active substance being incorporated in a polysaccharide matrix.

2. Description of the Related Art

Compositions for delayed release of an active substance, for example for delayed release of an enzyme for oral administration in the gastrointestinal tract of a mammal, have advantages, inter alia because the administration of the active substance can take place in a small number of doses and because a more constant concentration is obtained in the target environment.

Compositions for delayed release are known in diverse forms. One form of delayed release can comprise the presence of a matrix containing the active substance therein, which matrix slowly dissolves in the aqueous environment and thus releases the active substance in a delayed manner; a composition of this type is, for example, disclosed in European Patent Application EP-A-241179. A composition of this type in which the matrix is formed by a natural polysaccharide such as xanthan is disclosed in International Patent Application WO-A-87,05212. According to a variant thereof, the active substance is packaged in an insoluble capsule which is provided with a water-soluble stopper, as disclosed, inter alia, in British Patent Application 2,241,485.

Another form of a composition for delayed release is a composition from which the active substance is released by erosion, as is disclosed, for example, in European Patent Application EP-A-381182.

Compositions for delayed release in which the matrix material is a β-glucan, such as cellulose or a cellulose derivative, are disclosed, inter alia, in International Patent Application WO-A-88,10284 and Netherlands Patent Application 87,02294 (=GB-A-2,195,893). The use of heat-modified starch as the matrix for the controlled release of medicaments for oral administration is described by J. Herman and J. P. Remon, Int. J. Pharmaceutics, 56, 51–63 and 65–70 (1989).

The known compositions for the delayed release of an active substance frequently have the disadvantage that release is possible only for substances dissolving in the environment or effectively diffusing through the matrix material. Furthermore, the active substance of the known compositions does not normally proceed in accordance with an ideal zero order rate, that is to say with a constant amount per unit time, but in accordance with a first order rate, that is to say with an amount which decreases per unit time, or poorer; in addition, the materials used as matrix are often expensive.

SUMMARY OF THE INVENTION

The object of the invention is to provide a composition, and a method for the preparation thereof, which releases an active substance in a delayed manner and within a predetermined period of time, which further is harmless to health and/or the environment and which, moreover, is economical in use. The composition should especially be suitable for delayed release of active substances having a high molecular weight, which moreover are sensitive under certain conditions, such as a low pH or at increased environment temperatures.

This object is achieved by means of a composition according to the invention which to this end is characterised in that the matrix material in which the active substance is incorporated comprises an essentially crystalline straight-chain glucan and a glucan-degrading agent. The glucan is preferably an α-glucan and in particular an α-1,4-glucan and preferably has essentially a helical structure.

An α-1,4-glucan is understood to be an essentially straight-chain polysaccharide which is composed of anhydroglucose units which are linked to one another by α-bridges via the 1-position and 4-position. Other straight-chain glucans (polysaccharides) can also be used if these are able to assume a spiral-like structure, such as, for example, β-1,3-glucans.

DETAILED DESCRIPTION OF THE PREFERRED EMBODIMENT

Suitable α-1,4-glucans are in general starch fractions and starch derivatives. The α-1,4-glucan can, for example, be an amylose. Amylose is a straight chain of α-1,4-anhydroglucose units which has a degree of polymerisation (DP) of the order of 100–1,000. One form of amylose is so-called amylose V (Avebe), an amylose which has an amorphous structure and is precipitated from an aqueous solution by magnesium sulphate. Preferably, use is made of a product having a crystalline structure which can be derived from amylose V. This so-called helical amylose or crystalline amylose can be obtained from amylose by dissolving in water and complexing with a complex-forming agent such as 1-butanol, after which the complex-forming agent can be removed by careful spray-drying or by treatment with a suitable solvent, such as ethanol, methanol or acetone. The fractionation of amylose using complex-forming agents is described by W. Dvonch et al., J. Am. Chem. Soc., 72, 1748–1750 (1950) and S. Lanksy et al. ibid., 71, 4066–4075 (1949).

The crystalline and/or helical amylose to be used in the compositions according to the invention can also be obtained directly from starch, in a similar process using a complexing agent, further including washing the complex to remove amylopectin.

Suitable complexing agents for preparing crystalline, helical amylose by precipitating amylose from an aqueous solution are known in the art. They include 1,1,2,2-tetrachloroethane, cyclohexane, 1,1,1-and 1,1,2-trichloroethane, benzene, chloroform, fluorobenzene, o-xylene, 2,3-dimethylbutane, $C_3$–$C_8$ alcohols and phenols, such as butanol, amyl alcohol, cyclohexanol, hexanol and 2-octanol, isopropyl ketone, quinoline, chloral hydrate, butyric acid etc. See e.g. J. Muetgeert, Advances in Carbohydrate Chemistry, Vol. 16 Ed. Melville, Wolfrom, Acad. Press (1961).

Derivatives which are obtained by debranching branched glucans, in particular amylopectins, are also suitable. To this end the α-1,6 bonds of amylopectin are broken, preferably enzymatically (see Kobayashi, S. et al., Cereal Chem. 63, 71–74 (1968) and Netherlands patent 160,615) with the formation of amylodextrin, a straight-chain dextrin. This has a chain length (DP) of the order of 15–75, with a maximum between 15 and 25 and a maximum between 45 and 75. Amylodextrin, like the amylose V helix, occurs in the helix form with approximately 6 to 7 anhydroglucose units per winding.

The crystalline α-1,4-glucans suitable for use in the present compositions can be distinguished from unsuitable types of glucans by their infrared spectrum. The crystalline amylose and amylodextrin, just like cyclodextrin, have sharp absorptions at about 1150, 1080 and 1020 $cm^{-1}$, whereas amorphous amylose only exhibits broad or undistinguished absorptions at these frequencies.

The glucan-degrading agent is chosen as a function of the intended use of the composition. If used for release in the digestive tract of mammals, including man, the degrading agent is preferably an amylase and in particular α-amylase, an enzyme which normally cleaves starch. Thus the composition can pass the acid conditions of the stomach without hindrance, whereafter, under more neutral conditions, the glucan is degraded and the active substance is gradually released.

Surprisingly, it has been found that tablets and other administration forms which comprise such crystalline straight-chain glucans as matrix-forming material in combination with a glucan-degrading agent, are subject to little or no disintegration under certain conditions and can still disintegrate under other conditions. It is also surprising that the administration forms suffer little or no attack by externally present α-amylase, for example in the gullet, or by acid either. In addition, the tablets are found to be resistant to breaking and often more resistant to breaking than microcrystalline cellulose (for example Avicel®).

Preferably, the matrix material contains at least 5% by weight of water. If the material contains less than 5% of water, a usable release pattern is obtained but the strength is then no better than that, or even worse than that, of microcrystalline cellulose. Preferably, the material contains no more than 25% by weight, and more preferably no more than 20% by weight of water. In particular, the matrix material contains 7–16% by weight of water.

In addition, the matrix material can contain other fillers and auxiliaries. Thus, the presence of amylose not having a helix structure up to a content of, for example, 40% by weight does not interfere. Many types of starch contain about 25% of amylose and this therefore does not have to be removed if the starch is used as starting material for the matrix-forming material. Usable auxiliaries are the auxiliaries known per se for compositions of active substances, such as lubricants, for example magnesium stearate, co-solvents, pH regulators, preservatives, disintegrating agents, colorants, flavourings and the like.

Auxiliaries which modify the release pattern of the active substance from the matrix, such as auxiliaries which in themselves are inactive, for example lactose, can also advantageously be present.

The active substance can be present in the matrix material in virtually any desired concentration. The chosen concentration is largely determined by the intended use and the type of active substance. Thus, low concentration will suffice in many instances in case of enzymes. In general, the amount of active substance can make up, for example, 0.01–80% by weight of the composition, partly depending on the desired dosage. More particularly, the amount is between 0.05 and 25% by weight. Within this range, a release rate is obtained which is independent of the remaining amount of active substance, that is to say which has a zero order curve at least during the first part of the release period, example for 4 to 6 hours. This is also an unexpected aspect of the compositions according to the invention.

The rate of release of the composition according to the invention can be adjusted by varying one or more of the following parameters: active substance concentration in the matrix material, dosage unit form, in particular the surface area/capacity ratio, force under which the composition has been pressed, concentration of the glucan-degrading agent, or presence of disintegration-retarding agents, such as a coating or an inert filler.

The active substance can be of diverse natures. Examples are medicaments for oral, rectal, vaginal or transdermal administration, diagnostic agents, feedstuffs or conditioning agents, flavourings, manure or nutrients to be added to water or soil, preservatives, vaccine substances, hormones, genetic material, pesticides, attractants, growth promoters and the like. The active substances are also understood to comprise microorganisms, such as yeasts, moulds, bacteria and viruses and derivatives thereof. Mixtures of active substance can also be administered by means of the composition according to the invention. Release can take place in an aqueous medium, such as the gastrointestinal tract of animals, or in plants or in the soil.

The composition according to the invention is suitable, in particular, for the controlled release of substances of high molecular weight, such as more than 1,000 dalton, particularly more than 1,500 dalton, or even more than 5,000 dalton, and, in addition, substances which are poorly soluble in water. Examples thereof are proteins, such as enzymes, allergens, vaccine substances and oligosaccharides.

The composition can also be provided with a coating which ensures provides further protection or further delay of the release or, for example, has a colouring or taste function. The composition can also be in the form of a capsule in which the matrix material containing active substance is present, for example in granular form or powder form.

The composition according to the invention can be in any desired form, such as tablets, powders, granules, and implants.

Tablets can be pressed directly after mixing the active substance with the crystalline glucan as matrix material and any other auxiliaries. Preferably, however, the mixture is granulated before or after physical mixing of the active substance and matrix material and is then tableted.

As a result of the delayed release, the active substance can pass the acid conditions of, for example, the stomach, before the substance is released to the human or animal intestinal system.

EXAMPLES

Example I

A physical mixture of amylodextrin and α-amylase (Dexlo P®) was prepared in a round-bottomed flask by stirring for 20 minutes. The amylase concentration was 0.5 and 2.0 wt. %. A blank (without amylase) was also prepared. Tablets having a weight of 300 mg, a diameter of 13 mm and a surface of 1.3 $cm^2$ were pressed from the mixture using a pressing force of 50 kN during 5 minutes. Erosion of the tablets was determined in an conical flask containing 50 ml of PBS (phosphate-buffered saline) of pH 7.0. After agitating at ambient temperature for 18 hours (150 rpm), the blank tablet was hardly eroded, the tablet containing 0.5% of amylase was eroded for about 75% and the tablet containing 2.0% of amylase was completely eroded.

Example II

A physical mixture of amylodextrin and enzymes (Dexlo P®) was prepared in a round-bottomed flask by stirring for 20 minutes. Tablets having a weight of 300 mg, a diameter of 13 mm and a surface of 1.3 cm² were pressed from the mixture using a pressing force of 100 kN during 10 minutes.

The tablets of 300 mg had the following compositions:

T1 amylodextrin+6 mg of amylase (2%)+66 mg of cellulase (22%);

T2 amylodextrin+6 mg of amylase (2%)+15 mg of xylanase (5%);

T3 amylodextrin+6 mg of amylase (2%)+0.3 mg of glucose oxidase (0.1%);

as well as the following blanks:

B1 amylodextrin+66 mg of cellulase (22%);

B2 amylodextrin+15 mg of xylanase (5%);

B3 amylodextrin+0.3 mg of glucose oxidase (0.1%).

Erosion of the tablets was determined in 20 ml of 0.1 mole/1 PBS (phosphate-buffered saline) of pH 7.0, saturated with oxygen. The enzyme activity (tables 1, 2 and 3) and the protein concentration (table 4) of 1 ml samples were determined at various intervals, using the following methods:

Cellulase: substrate carboxymethylcellulose, reducing sugar, according to N. Nelson: A Photometric Adaptation of the Somogyi Method for the Determination of Glucose; *J. Biol. Chem.* 103 375–380 (1944);

Xylanase: substrate xylan, reducing sugar, according to Nelson-Somogyi (see above);

Glucose oxidase: R. L. Kelley and C. A. Reddy, Glucose Oxidase of *Phanerochaete chrysosporium*, from Methods in Enzymology V161, Biomass Part B, Academic Press, New York, 1988.

Protein: BCA Protein Assay Kit (Pierce).

TABLE 1

Reducing Power (U) in cellulase assay of tablets T1-2 and B1-2

| Time (h) | T1 | B1 | T2 | B2 |
|---|---|---|---|---|
| 0 | 1.60 | — | 0.40 | — |
| 3 | 43.0 | 9.80 | 13.7 | 2.80 |
| 5 | 56.2 | — | 20.0 | — |
| 7 | 65.0 | — | 30.7 | — |
| 22 | 83.9 | >13.2 | 55.2 | 12.1 |

—: not measured

TABLE 2

Reducing power (U) in xylanase assay of tablets T1-2 and B1-2

| Time (h) | T1 | B1 | T2 | B2 |
|---|---|---|---|---|
| 0 | 7.20 | — | 1.66 | — |
| 3 | 174.2 | 88.0 | 24.4 | 8.20 |
| 5 | 235.8 | — | 48.9 | — |
| 7 | 254.1 | — | 62.7 | — |
| 22 | 286.5 | 158.7 | 127.3 | 29.3 |

—: not measured

TABLE 3

Glucose oxidase activity (U) of tablets T3 and B3

| Time (h) | T3 | B3 |
|---|---|---|
| 0 | 0.00 | — |
| 1 | 1.42 | — |
| 3 | 3.40 | 0.011 |
| 5 | 9.22 | — |

TABLE 3-continued

Glucose oxidase activity (U) of tablets T3 and B3

| Time (h) | T3 | B3 |
|---|---|---|
| 7 | 11.8 | — |
| 22 | — | 0.031 |

—: not measured

TABLE 4

Total amount of released protein form tablets T1-2 and B1-2

| Time (h) | T1 (mg) | B1 (mg) | T2 (mg) | B2 (mg) |
|---|---|---|---|---|
| 0 | 0.30 | — | 0 | — |
| 3 | 25.9 | 11.9 | 1.39 | 0 |
| 5 | 30.6 | — | 4.45 | — |
| 7 | 36.1 | — | 6.44 | — |
| 22 | 39.9 | 21.1 | 9.94 | 3.78 |

—: not measured

Example III

Tablets with 66 mg of cellulase and 15 mg of xylanase respectively were pressed at 100 kN/10 minutes following the procedure of Example II. The release pattern was determined in the manner mentioned in Example II: (a) directly at pH 7.0 and (b) at pH 7.0 after incubation for one hour at pH 2.0. The change of activity, measured from the reducing power, of the cellulase tablet is shown in table 5, and of the xylanase tablet in table 6. The tablets appear to be effectively acid-resistant.

TABLE 5

Comparison of the reducing power in cellulase and xylanase assays of cellulase tablet with and without acid treatment

| Time | cellulase assay | | xylanase assay | |
|---|---|---|---|---|
| (h) | pH 2 → 7 | pH 7 | pH 2 → 7 | pH 7 |
| 0 | 0.34 | 2.40 | 3.40 | 13.40 |
| 1 | 4.01 | 8.10 | 21.45 | 44.37 |
| 2 | 16.79 | 15.84 | 64.11 | 74.79 |
| 3 | 16.96 | 17.54 | 94.70 | 97.06 |
| 4 | 20.64 | 21.38 | 108.00 | 111.80 |

TABLE 6

Comparison of the reducing power in xylanase and cellulase assays of xylanase tablet with and without acid treatment

| Time | xylanase assay | | cellulase assay | |
|---|---|---|---|---|
| (h) | pH 2 → 7 | pH 7 | pH 2 → 7 | pH 7 |
| 0 | 2.78 | 4.60 | 0 | 0.64 |
| 1 | 4.32 | 9.16 | 0.61 | 2.84 |
| 2 | 10.21 | 19.96 | 3.25 | 7.54 |
| 3 | 23.69 | 33.90 | 9.87 | 13.92 |
| 4 | 35.69 | 51.20 | 15.10 | 18.97 |

Example IV

Tablets of 600 mg containing 1 mg of yeast cells (*Saccharomyces cerevisiae*, $10^7$ cells per tablet) in amylodextrin/α-amylase were pressed using a force of 5 kN during 20 sec. according to Example II. The tablets were given different pretreatments and were subsequently brought in an aqueous phosphate buffer having pH 7. At this pH, the tablets disintegrate after 1 hour, releasing the yeast cells. The viability was checked by counting the colony forming units (cfu). The results are summarised in table 7.

TABLE 7

| run | pretreatment | | treatment | cell number |
|-----|------|------|------|------|
|  | head | acid | pH = 7 | (cfu/ml) |
| 1 | pure yeast extract | | 1 h | $1.3*10^4$ |
| 2 | tablet without yeast | | 1 h | <1 |
| 3 | 85° C./30 s | — | 1 h | $1.8-2.6*10^4$ |
| 4 | 85° C./60 s | — | 1 h | $1.0-1.1*10^4$ |
| 5 | 85° C./60 s | pH = 2/1 h | 1 h | $0.75*10^4$ |
| 6 | — | pH = 2/1 h | 1 h | $0.86-1.2*10^4$ |

Table 7 shows that the tablets prepared according to the invention are resistant to both heat and acid for some time; the acid treatment simulates a passage through the stomach. Disintegration of the tablet at neutral pH releases viable cells.

Example V

Preparation of amylose with a helical structure (metastable form):
a) Starch fractionation:
In 1 liter of water containing 22 ml of 2-methyl-1-butanol, 100 g of starch is dissolved at 160° C. For stabilisation of the starch 0.1 wt. % of sodium sulphite is added. After cooling the solution the crystalline amylose-methylbutanol complex precipitates. The precipitate is collected by centrifugation and washed several times with a solution of 2-methyl-1-butanol in order to remove the amylopectin (being dissolved). The water in the complex is subsequently removed by washing the complex with ethanol en centrifugation (first time) or filtration. In this way the complex is converted to the crystalline amylose-ethanol complex. the so-called metastable form (so-called because the amylose in this form is temporarily soluble in cold water) is obtained by removing the ethanol in vacuo (1 mm Hg) at 50° C. in the presence of phosphorus pentaoxide.
b) Amylose fractionation:
In amylose is chosen as raw material the washing steps needed to remove the amylopectin may be omitted. For the remainder, the procedure is similar as described above.

It may be noted that many other complexing agents may be used instead of 2-methyl-1-butanol. However, the critical concentration of each complexing agent should be taken into account: with starch the critical concentration is used, and with amylose the critical or a higher concentration may be used. The critical concentration of a number of some complexing agents is summarised below (form J. Muetgeert, Advances in Carbohydrate Chemistry, Vol. 16, pp. 300–305 (1961)): complexing agent (critical concentration in g per 100 ml of water):

| | |
|---|---|
| 1-butanol (4.2) | isopropyl ketone (0.6) |
| amyl alcohol (1.8) | cyclohexanol (0.5) |
| 1-hexanol (0.3) | phenol (2.5) |
| 2-octanol (0.04) | quinoline (0.6) |
| chloral hydrate (5-8) | butyric acid (11) |

Similar tablets as those illustrated in Examples I–IV can be prepared using helical amylose instead of amylodextrin; similar results are obtained.

We claim:

1. A composition for the delayed release of an active substance, the active substance being present in an amount of 0.01–80% by weight of the composition and being incorporated in a polysaccharide matrix, the matrix comprising at least 35% by weight of a crystalline straight-chain α-glucan having a helix structure, and a glucan-degrading agent present in the amount of 0.05–15% by weight of the composition.

2. A composition according to claim 1, in which the matrix material comprises amylodextrin or a fraction obtained from amylose which has a helix structure.

3. A composition according to claim 1, wherein the glucan-degrading agent is α-amylase.

4. A composition according to claim 1, wherein the active substance is present in an amount of 0.05–25% by weight.

5. A composition for the delayed release of an active substance being a compound, the active substance having a molecular weight of more than 1,500 dalton and being present in an amount of 0.01–80% by weight of the composition and being incorporated in a polysaccharide matrix, the matrix comprising at least 35% by weight of a crystalline straight-chain α-glucan having a helix structure, and a glucan-degrading agent.

6. A composition according to claim 5, in which the matrix material comprises amylodextrin or a fraction obtained from amylose which has a helix structure.

7. A composition according to claim 5, in which the glucan-degrading agent is α-amylase.

8. A composition according to claim 5, which contains 0.05–15% by weight of the glucan-degrading agent.

9. A composition according to claim 5, in which the active substance is present in the amount of 0.05–25% by weight.

10. A composition for the delayed release of an active substance, the active substance being a protein or a microorganism and being present in an amount of 0.01–80% by weight of the composition and being incorporated in a polysaccharide matrix, the matrix comprising at least 35% by weight of a crystalline straight-chain α-glucan having a helix structure, and a glucan-degrading agent.

11. A composition according to claim 10, in which the matrix material comprises amylodextrin or a fraction obtained from amylose which has a helix structure.

12. A composition according to claim 10, in which the glucan-degrading agent is α-amylase.

13. A composition according to claim 10, which contains 0.05–15% by weight of the glucan-degrading agent.

14. A composition according to claim 10, in which the active substance is present in an amount of 0.05–25% by weight.

15. A composition according to claim 10, in which the active substance is a compound having a molecular weight of more than 1,500 dalton.

16. A method for the preparation of a composition for the delayed release of an active substance, the active substance being incorporated in a polysaccharide matrix and the matrix comprising at least 35% by weight of a crystalline straight-chain α-glucan having a helix structure, and a glucan-degrading agent, the method comprising granulating said α-glucan and mixing the granulated said α-glucan, before or after granulating, with said active substance and the glucan-degrading agent such that the active substance is present in the amount of 0.01–80% by weight of the composition, and then bringing the granulated mixture to a desired form.

* * * * *